United States Patent [19]
Kim et al.

[11] Patent Number: 5,674,897
[45] Date of Patent: Oct. 7, 1997

[54] MATERIALS AND METHODS FOR CONTROLLING NEMATODES

[75] Inventors: Leo Kim, Carlsbad; Jerald S. Feitelson, San Diego; John Harvey, Escondido; Paul S. Zorner, Carlsbad, all of Calif.

[73] Assignee: Mycogen Corporation, San Diego, Calif.

[21] Appl. No.: 546,053

[22] Filed: Oct. 20, 1995

[51] Int. Cl.$^6$ .......................... A01N 37/00; A01N 37/02; A01N 37/06; A01N 43/08

[52] U.S. Cl. .......................... 514/552; 514/30; 514/450; 514/546; 514/547; 514/549; 514/557; 514/558; 514/560

[58] Field of Search .......................... 514/546, 549, 514/552, 547, 557, 558, 560, 30, 450

[56] References Cited

U.S. PATENT DOCUMENTS

| | | | |
|---|---|---|---|
| 2,852,426 | 9/1958 | Stansbury | 514/547 |
| 3,931,413 | 1/1976 | Frick et al. | 514/558 |
| 3,983,214 | 9/1976 | Misato et al. | 514/53 |
| 4,002,775 | 1/1977 | Kabara | 426/532 |
| 4,310,519 | 1/1982 | Albers-Schonberg et al. | 514/30 |
| 4,547,520 | 10/1985 | Ide et al. | 514/450 |
| 4,560,677 | 12/1985 | Dybas | 514/30 |
| 4,771,571 | 9/1988 | Obrero et al. | 47/58 |
| 4,948,734 | 8/1990 | Edwards et al. | 435/252.3 |
| 5,093,120 | 3/1992 | Edwards et al. | 514/2 |
| 5,151,363 | 9/1992 | Payne | 435/252.5 |
| 5,236,843 | 8/1993 | Narva et al. | 435/252.3 |
| 5,246,716 | 9/1993 | Sedun et al. | 424/713 |
| 5,270,448 | 12/1993 | Payne | 530/350 |
| 5,281,530 | 1/1994 | Sick et al. | 435/252.3 |
| 5,284,819 | 2/1994 | Zorner et al. | 504/127 |
| 5,322,932 | 6/1994 | Narva et al. | 530/350 |
| 5,350,577 | 9/1994 | Payne | 514/2 |
| 5,426,049 | 6/1995 | Sick et al. | 435/252.3 |
| 5,439,881 | 8/1995 | Narva et al. | 514/2 |
| 5,602,107 | 2/1997 | Choi | 514/30 |

FOREIGN PATENT DOCUMENTS

| | | |
|---|---|---|
| 0094779 | 11/1983 | European Pat. Off. . |
| 0125155 | 11/1984 | European Pat. Off. . |
| 1581109 | 9/1969 | France . |
| 907842 | 10/1962 | United Kingdom . |
| 1219077 | 1/1971 | United Kingdom . |

OTHER PUBLICATIONS

Vrain, T.C. (1980) "Fatty acids and their derivatives for nematode control" *Journal of Nematology* 12(4):240.

Ahmed, S.M. et al. (1985) "Preparation and Characterization of Derivatives if Isoricinoleic Acid and Their Antimicrobial Activity" JAOCS 62(11):1578–1580.

Anderson, T.E. et al. (1986) "Avermectin B$_1$:Ingestion and Contact Toxicity Against *Spodoptera eridania* and *Heliothis virescens* (Lepidoptera:Noctuidae) and Potentiation by Oil and Piperonyl Butoxide" Journal of Economic Entomology 79(1):197–201.

Bottjer, K.P. et al. (1985) "Nematoda: Susceptiblity of the Egg to *Bacillus thuringiensis* Toxins" Experimental Parasitology 60:239–244.

Burg, R.W. et al. (1979) "Avermectin, New Family of Potent Anthelmintic Agents: Producing Organism and Fermentation" Antimicrobial Agents and Chemotherapy 15(3):361–367.

Boyce Thompson Institute for Plant Reserch 58th Annual Report (1981) 44 pages.

Chase, A.R. et al. (1983) "Influence of an Insecticidal Soap on Several Foliar Diseases of Foliage Plants" Plant Disease 67:1021–1023.

Ciordia, H. et al. (1961) "A Preliminary Report on the Effects of *Bacillus thuringiensis* var. thuringiensis Berliner on the Development of the Free–Living Stages of Some Cattle Nematodes" Journal of Parasitology 47:41 (abstract only).

Coles, G.C. (1986) "Anthelmintic Resistance in Sheep" Veterinary Clinics of North America: Food Animal Practice 2(2):423–432.

Frick, E.L. et al. (1972) "Erdication of Apple Powdery Mildew From Infected Buds" Plant Disease Reporter 56(9):770–772.

Ignoffo, C.M. et al. (1977) "Deleterious Effects of the Thermostable Toxin of *Bacillus thuringiensis* on Species of Soilk–Inhabiting, Myceliophagus and Plant–Parasitic Nematodes" Journal of Kansas Entomological Society 50(3):394–398.

Kiuchi, F. et al. (1987) "Studies on Crude Drugs Effective on Visceral Larva Migrans. I. Identifiction of Larvicidal Principles in Betel Nuts" Chem. Pharm. Bull 35:2880–2886.

Malik, Z. et al. (1984) "Effect of pH and Some Mineral Salts and Fatty Acids on Survival of *Xiphinema americanum*" Nematol. medit. 12:73–79.

Prichard, R.K. et al. (1980) "The Problem of Anthelmintic Resistance in Nematodes" Australian Veterinary Journal 56:239–251.

Putter, I. et al. (1981) "Avermectins: novel insecticides, acaricides and nematicides from a soil microorganism" Experientia 37:963–964.

Sitaramaiah, K. et al. (1977) "Response of *Meloidogyne javanica* and Other Nematodes to Fatty Acids" Indian J. Nematol. 7:58–65.

Stadler, M. et al. (1994) "Fatty Acids and Other Compounds with Nematicidal Activity from Cultures of Basidiomycetes" Planta Med. 60:128–132.

Tarjan, A.C. et al. (1956) "Nematocidal Value of Some Fatty Acids" Agricultural Experiment Station, University of Rhode Island, Kingston, Bulletin 332, Contribution 884.

*Primary Examiner*—John Pak
*Attorney, Agent, or Firm*—Saliwanchik, Lloyd & Saliwanchik

[57] ABSTRACT

Methods and compositions for the control of nematodes are disclosed. Specifically, fatty acid ester compounds have been found to advantageously control nematodes at concentrations which are non-phytotoxic. The fatty acid ester compounds can be used in conjunction with other nematicidal agents such as free fatty acids, fatty acid salts, avermectins, ivermectin, and milbemycin.

10 Claims, No Drawings

MATERIALS AND METHODS FOR CONTROLLING NEMATODES

BACKGROUND OF THE INVENTION

Nematodes are important plant pests which cause millions of dollars of damage each year to turf grasses, ornamental plants, and food crops. Efforts to eliminate or minimize damage caused by nematodes in agricultural settings have typically involved the use of soil fumigation with materials such as chloropicrin, methyl bromide, and dazomet, which volatilize to spread the active ingredient throughout the soil. Such fumigation materials can be highly toxic and may create an environmental hazard. Various non-fumigant chemicals have also been used, but these too create serious environmental problems and can be highly toxic to humans.

The accepted methodology for control of nematodes afflicting animals has centered around the use of the drug benzimidazole and its congeners. The use of these drugs on a wide scale has led to many instances of resistance among nematode populations (Prichard, R. K. et al. [1980] "The problem of anthelmintic resistance in nematodes," Austr. Vet. J. 56:239–251; Coles, G. C. [1986] "Anthelmintic resistance in sheep," In *Veterinary Clinics of North America: Food Animal Practice*, Vol 2:423–432 [Herd, R. P., Eds.] W. B. Saunders, New York).

A small number of research articles have been published concerning the effects of δ-endotoxins from *B. thuringiensis* species on the viability of nematode eggs. See, for example, Bottjer, Bone and Gill ([1985] *Experimental Parasitology* 60:239–244); Ignoffo and Dropkin (Ignoffo, C. M., Dropkin, V. H. [1977] *J. Kans. Entomol. Soc.* 50:394–398); and Ciordia, H. and W. E. Bizzell ([1961] *Jour. of Parasitoloy* 47:41 [abstract]). Several patents have issued describing the control of nematodes with B.t. See, for example, U.S. Pat. Nos. 4,948,734; 5,093,120; 5,281,530; 5,426,049; 5,439,881; 5,236,843; 5,322,932; 5,151,363; 5,270,448; 5,350,577.

The pesticidal activity of avermectins is well known. The avermectins are disaccharide derivatives of pentacyclic, 16-membered lactones. They can be divided into four major compounds: $A_{1a}$, $A_{2a}$, $B_{1a}$, and $B_{2a}$; and four minor compounds: $A_{1b}$, $A_{2b}$, $B_{1b}$, and $B_{2b}$.

The organism which produces avermectins was isolated and identified as *Streptomyces avermitilis* MA-4680 (NRRL-8165). Characteristics of the avermectin producing culture and the fermentation process are well documented and known to those skilled in the art (Burg, R. W. et al. [1979] "Avermectins, New Family of Potent Anthelmintic Agents: Producing Organism and Fermentation," *Antimicrob. Agents Chemother.* 15(3):361–367). The isolation and purification of these compounds is also described in U.S. Pat. No. 4,310,519, issued Jan. 12, 1982.

Another family of pesticides produced by fermentation are the milbemycins, which are closely related to the avermectins. The milbemycins can be produced by a variety of Streptomyces and originally differed from the avermectins only in the C-13 position. The milbemycins and their many derivatives are also well known to those skilled in the art and are the subject of U.S. patents. See, for example, U.S. Pat. No. 4,547,520.

While the avermectins were initially investigated for their anthelmintic activities, they were later found to have other insecticidal properties, although the degree varies. The activity of avermectins must generally be determined empirically.

22,23-dihydroavermectin $B_1$ is a synthetic derivative of the avermectins and has been assigned the nonproprietary name of ivermectin. It is a mixture of 80% 22,23-dihydroavermectin $B_{1a}$ and 20% 22,23-dihydroavermectin $B_{1b}$. Ivermectin has been tested on a variety of laboratory and domestic animals for control of nematodes, ticks, and heartworms.

Avermectin $B_{2a}$ is active against the rootknot nematode, *Meloidogyne incognita*. It is reported to be 10–30 times as potent as commercial contact nematicides when incorporated into soil at 0.16–0.25 kg/ha (Boyce Thompson Institute for Plant Research 58th Annual Report [1981]; Putter, I. et al. [1981] "Avermectins: Novel Insecticides, Acaracides, and Nematicides from a Soil Microorganism," Experientia 37:963–964). Avermectin $B_{2a}$ is not toxic to tomatoes or cucumbers at rates of up to 10 kg/ha. Avermectin $B_1$ is a combination of avermectin $B_{1a}$ (major component) and avermectin $B_{1b}$. It has demonstrated a broad spectrum of insecticidal activities. The data indicate that avermectin $B_1$ is primarily a miticide, although it is also effective on the Colorado potato beetle, potato tuberworm, beet armyworm, diamondback moth, gypsy moth, and the European corn borer.

The use of avermectins in various agricultural applications has been described in publications and patents. The use of avermectin with spray oils (lightweight oil compositions) has been described. See, for example, U.S. Pat. No. 4,560,677 issued Dec. 24, 1985; EPO applications 0 094 779 and 0 125 155; and Anderson, T. E., J. R. Babu, R. A. Dybas, H. Mehta (1986) *J. Econ. Entomol.* 79:197–201.

Fatty acids are a class of natural compounds which occur abundantly in nature and which have interesting and valuable biological activities. The in vitro activity of fatty acids against many medically important fungi and bacteria is well known. There is a much smaller body of literature concerning the activity of fatty acids and their derivatives against pathogens on agricultural crops. Ahmed et al. (Ahmed, S. M., F. Ahmad, S. M. Osman [1985] *JAOCS* 62:1578–1580) report in vitro inhibition of radial growth of several fungal genera with plant pathogenic representatives. Recently there has been an expanding use of "insecticidal soaps" in agriculture which are salts of certain fatty acids. Chase et al. (Chase, A. R., L. S. Osborne [1983] *Plant Disease* 67:1021–1023) observed that applications of an 18:1 fatty acid salt "insecticidal soap" gave moderate preventive control of two foliage plant diseases and actually exacerbated two other diseases. Nickel and silver salts of fatty acids have been used to control pathogens on plants: GB Patent Nos. 907,842 and 1,219,077. In U.S. Pat. No. 3,983,214, Misato et al. claim a fungicidal composition containing a sucrose fatty acid ester. In U.S. Pat. No. 4,771,571, Obrero et at describe a method of preventing infections of pineapple by treating the fruit, while on the bush, with a surfactant. In U.S. Pat. No. 4,002,775, Kabara et al. claim microbicidal food additives comprising 1 or 2-mono-laurin polyol ester. The use of fatty acid esters and alcohols for the control of powdery mildew on apple buds has been described (Frick, E. L., R. T. Burchill [1972] *Plant Disease Reporter* 56:770–772; U.S. Pat. No. 3,931,413). In the '413 patent, Frick et al. emphasize the phytotoxicity of fatty acids and state that the acid or salt form should only be used on dormant plant tissue. The phytotoxicity of fatty acids and their salts is well documented and has long been believed to be a barrier to the use of these compositions on living plants. See U.S. Pat. No. 5,246,716. Tarjan and Cheo (Tarjan, A. C., P. C. Cheo [1956] "Nematocidal Value of Some Fatty Acids," Bulletin 332, Contribution 884, Agricultural Experiment Station, University of Rhode Island, Kingston, 41 pp.) report the activity of certain fatty acids against nematodes. Tarjan and Cheo do not disclose or suggest the use of fatty acid esters. In 1977 Sitaramaiah and Singh (Sitaramaiah, K, R. S. Singh [1977] *Indian J. Nematol* 7:58–65) also examined the response of nematodes to fatty acids. These researchers examined the effects of low molecular weight acids such as acetic, formic, propionic, and buryrio acids. The results of these tests with short chain acids were equivocal, showing nematode-inhibitory action in some instances and stimulatory activity in other instances. Phytotoxicity of these acids was observed at higher concentrations. These short chain fatty acids were also examined by Malik and Jairajpuri (Malik, Z., M. S. Jairajpuri [1977] *Nematol. medit.* 12:73–79), who observed nematode toxicity at high concentrations of the fatty acids. In 1987, Kiuchi et al. (Kiuchi, F., N. Miyashita, Y. Tsuda, K. Kondo, H. Yoshimura [1977] *Chem. Pharm. Bull.* 35:2880–2886) reported the anthelmintic effect of fatty acids obtained from betel nuts. The fatty acids were found to be toxic against larvae of worms which cause parasitic diseases in humans and animals. Stadler et al. (Stadler, M., A. Mayer, H. Anke, O. Sterner [1994] *Planta Med.* 60:128–132) studied fatty acids and other compounds with nematicidal activity which could be obtained from cultures of Basidiomycetes. Stadler et al. primarily evaluated long chain fatty acids having, for example, 16 to 18 carbons.

Fatty acid ester compositions have been described in U.S. Pat. No. 5,284,819, but this patent does not disclose or suggest the use of fatty acid esters to control nematodes.

BRIEF SUMMARY OF THE INVENTION

The subject invention concerns compositions and processes for controlling nematodes. In one embodiment, the subject invention comprises the use of certain fatty acid compounds to control nematodes which infest plants or the situs of plants. Nematodes afflicting animals can also be controlled using the methods and compositions of the subject invention. The fatty acid compounds useful according to the subject invention can be from about C8 to about C14 and can be, for example, in the epoxide, cyclopropane, methylated, or hydroxylated forms. In a preferred embodiment of the subject invention, fatty acid esters are used.

Preferred fatty acid esters useful according to the subject invention can be represented by the following formula:

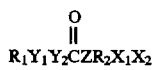

wherein

Z=O, N, or S $R_1$=C7 to C13 saturated or unsaturated hydrocarbon, or an epoxide, or cyclopropane thereof $Y_1$=H, C1–C5 hydrocarbon, or hydroxyl at any position along $R_1$ $Y_2$=H, C1–C5 hydrocarbon, or hydroxyl at any position along $R_1$ $R_2$=C1 to C10 saturated or unsaturated hydrocarbon $X_1$=H, hydroxyl, or C1 to C3 hydrocarbon at any position along $R_2$ $X_2$=H, hydroxyl, or C1 to C3 hydrocarbon at any position along $R_2$.

In a preferred embodiment of the subject invention, a C8 to C14 fatty acid ester is used. Advantageously, the ester may be a methyl ester or ethylene glycol ester.

The invention process is particularly valuable to control nematodes attacking the roots of desired crop plants, ornamental plants, and turf grasses. The desired crop plants can be, for example, tomatoes, potatoes, or strawberries.

In one embodiment of the subject invention, the fatty acid compound is used in conjunction with another nematicidal agent. The other nematicidal agent may be, for example, a biological agent, an avermectin, or a milbemycin.

DETAILED DISCLOSURE OF THE INVENTION

The process of the subject invention concerns the use of fatty acid compounds to control the infestation of plants or animals by nematodes. In a preferred embodiment of the subject invention, the fatty acid compound is a C8 to C14 fatty acid ester. C9 to C12 fatty acid esters are particularly preferred. The fatty acid esters used according to the subject invention can be unsubstituted, or substituted, saturated, or unsaturated. The fatty acid component used according to the subject invention may be a single fatty acid ester or a mixture of two or more fatty acid esters. The fatty acid ester may be used in conjunction with other fatty acid compounds, including the free acids and salts. The salts may be, for example, sodium or potassium salts, or ammonium salts.

Fatty acid compounds specifically exemplified herein include the methyl ester of pelargonic acid (PAME), ethylene glycol ester of pelargonic acid (PAEGE), and methyl ester of laurie acid (C12) (LAME).

The fatty acid compounds used in the invention can be applied to animals, plants, or to the situs of plants needing nematode control. The fatty acid compositions may be applied by, for example, drip and drench techniques. With the drip application, the fatty acid composition can be applied directly to the base of plants or to the soil immediately adjacent to the plants. The composition may be applied through already existing drip irrigation systems. This procedure is particularly applicable for ornamental plants, strawberries, tomatoes, potatoes, and vegetables. Alternatively, a drench application can be used. For plants, a sufficient quantity of the fatty acid composition is applied such that the composition drains to the root area of the plants. An important aspect of the subject invention is the surprising discovery that certain fatty acid compounds have excellent nematicidal activity at concentrations which are not phytotoxic. The drench technique can be used for a variety of crops and for turf grasses. The drench technique can also be used for animals. Preferably, the fatty acid composition would be administered orally to facilitate activity against internal nematode parasites. The compositions of the subject invention can readily be applied using the teachings provided herein.

In a preferred embodiment of the subject invention, a fatty acid ester compound will be applied as an aqueous microemulsion. As described herein, the concentration of the fatty acid ester should be sufficient to control the nematode infestation without causing phytotoxicity to the desired plants. The concentration of fatty acid ester may be, for example, from about 0.001% to about 2%, preferably from about 0.025% to about 1%, and, most preferably, from about 0.05% to about 0.5%. The concentration of the fatty acid ester can be reduced by using the ester in conjunction with another fatty acid compound such as the free fatty acid or a salt.

The fatty acid composition used according to the subject invention can be applied in conjunction with another nematicidal agent. The second nematicidal agent may, for example, be applied simultaneously or sequentially with the fatty acid ester. Such other nematicidal agents include, for example, avermectins. The avermectin compound used according to the subject invention may be any of the avermectins, milbemycins, or derivatives of either, having activity against nematodes. The avermectin's activity will be enhanced when combined with a fatty acid compound as described herein. Thus, the specific combination of ingredients can be manipulated to provide the optimal composition for a particular application.

Standard concentrations of avermectins are well known to those skilled in the art. For example, the avermectin compounds can be employed in the combination of the subject invention at concentrations of from about 0.03 to about 110 parts per million (ppm). Preferably, from about 1 to about 5 ppm are employed.

As would be readily appreciated by a person skilled in the art, the delivery of the fatty acid and/or avermectin compound can be calculated in terms of the active ingredient applied per unit area. For example, the fatty acid may be applied at a rate of about 0.02 lb/acre to about 0.1 lb/acre and, preferably, from about 0.5 lb/acre to about 2 lbs/acre. Similarly, the avermectin product can be applied at a rate of up to about 16 oz. of formulated product ("AVID," available from Merck) per acre. Preferably, about 4 oz. to about 8 oz. formulated "AVID" per acre would be used. Thus, the avermectin compound can be applied up to about 0.02 lb/acre. Preferably, the rate of avermectin is between about 0.005 lb/acre and 0.01 lb/acre. A person of ordinary skill in the art would readily appreciate that the desired application rate of the active ingredients could be achieved using a great variety of different concentrations of active ingredients while varying the application rate of the solution. Thus, a large quantity of dilute solution could be applied or a smaller quantity of a more concentrated solution.

A variety of different avermectins or related compounds can be used according to the subject invention. Ivermectin may also be used according to the subject invention, as may the milbemycins. For brevity, the term "avermectin" is used herein to refer to all the avermectins and their derivatives as well as related compounds such as the milbemycins and the ivermectins. "Derivatives" refer to chemical modifications of the avermectins or milbemycins which are well known and available to those skilled in this art. Such derivatives are described, for example, in U.S. Pat. No. 4,560,677. Avermectin is readily available under a variety of tradenames including "AVID," "ZEPHYR," "VERTIMEC," and "AGRI-MEK."

The fatty acid compositions of the subject invention may also be used in conjunction with nematicidal agents other than the avermectins. For example, the fatty acid compounds may be used with biological agents such as *Bacillus thuringiensis* or with nematicidal fungi. In this context, the fatty acid composition could be applied at concentrations which would not antagonize the action of the biological agent. The biologically active agent may be in a live proliferative form or may be in a dead stabilized form as described, for example, in U.S. Pat. Nos. 4,695,462 and 4,695,455. Furthermore, the fatty acid compositions of the subject invention may be used with plants which are specifically bred or engineered for nematode resistance. The plants may, for example, be transformed with B.t. genes which confer nematode resistance or may simply be hybrids or varieties selected for such resistance. The fatty acid compositions of the subject invention are particularly effective against free-living ectoparasitic nematodes and, therefore, combined use with plants selected for endoparasitic nematode resistance is highly advantageous.

Following are examples which illustrate procedures for practicing the invention. These examples should not be construed as limiting. All percentages are by weight and all solvent mixture proportions are by volume unless otherwise noted.

EXAMPLE 1

Preparation of Fatty Acid Esters

Synthesis of ethylene glycol monopelargonate. 51.5 g pelargonic acid, and 51 g ethylene glycol were dissolved in 200 ml of dichloromethane, and 20 drops of $H_2SO_4$ were added to the mixture. It was stored at room temperature for 6 days. After 6 days, 150 ml of 0.1N NaOH was added to the reaction mixture, which was then vigorously shaken. The dichloromethane layer (lower layer) was collected and washed with saturated NaCl solution.

After drying on $Na_2SO_4$, the chloroform layer was evaporated. Remaining oil (38 g) was subjected to vacuum distillation, yielding 34.8 g (yield 53.8%) of ethylene glycol monopelargonate (b.p. 135°–137° C. [7 mm Hg]).

Synthesis of methyl ester of pelargonic acid. The methyl ester of pelargonic acid can readily be produced using procedures well known to those skilled in the art. One such procedure would be analogous to that used to produce the ethylene glycol monopelargonate. For example, about 51 g of pelargonic acid and 51 g of methyl alcohol can be dissolved in about 200 ml of dichloromethane to which 20 drops of $H_2SO_4$ are added. The mixture can be stored at room temperature for 6 days, at which time 150 ml of NaOH is added to the reaction mixture, which is then vigorously shaken. The dichloromethane layer (lower layer) is collected and washed with saturated NaCl solution.

After drying on $Na_2SO_4$, the chloroform layer is evaporated. Remaining oil is then subjected to vacuum distillation, yielding the methyl ester of pelargonic acid.

Synthesis of the esters of $C_6$ to $C_{14}$ acids.

(a) Hexanoic acid ($C_6$ acid) and heptanoic acid ($C_7$ acid)—each of 100 mmol of $C_6$ and $C_7$ acids were added to 300 mmol of ethylene glycol. Several drops of $H_2SO_4$ were added to the mixture and stored at room temperature for 9 days. Isolation of the esters can be carried out using the same procedure as that to isolate ethylene glycol monopelargonate.

(b) Decanoic acid ($C_{10}$ acid), dodecanoic acid ($C_{12}$ acid), and tetradecanoic acid ($C_{14}$ acid)—each of 100 mmol of $C_{10}$, $C_{12}$ and $C_{14}$ acids were dissolved in 50 ml dichloromethane, and 300 mmol of ethylene glycol were added to the solutions. Several drops of $H_2SO_4$ were added to the mixture. The reaction mixtures were stored at room temperature for 9 days. Isolation of the esters were carried out using the same procedure as that to isolate ethylene glycol monopelargonate.

A variety of fatty acid esters useful according to the subject invention can be readily prepared by a person skilled in this art having the benefit of the subject disclosure.

EXAMPLE 2

Nematicidal Activity of Fatty Acid Compositions

*Caenorhabditis elegans* was grown for 5 days at 18° C., 150 rpm, feeding on *E. coli* strain MC1061 in submerged batch culture in 2 L flasks according to *The Nematode Caenorhabditis elegans* (1988) Cold Spring Harbor Laboratory Press, p. 602.

Ten milliliters of culture were removed, briefly centrifuged (1,500 rpm, 2 minutes, room temperature) and the nematodes resuspended in 10 ml of M9 broth. One and a half milliliters of nematodes were added to 9.3 ml of stationary phase MC1061 *E. coli* cells in L-broth, and divided into 150 µl aliquots in 24-well tissue culture plates. Each well contained approximately 25 mixed stage (L1-adult hermaphrodite) nematodes.

To each well, 150 µl of fatty acid dilutions or controls were added and quickly mixed by gentle swirling. Nematode viability was scored by visual examination under a 10× dissecting microscope, and prodding with 31-gauge platinum wire. A 5-point scoring system was used as follows:

1: no effect
2: <10% dead, some ring-shaped worms, mostly highly active
3: some motile worms, most stiff and immobile
4: >90% stiff and immobile (a few twitching larvae)
5: 100% stiff and immobile, no signs of life.

Intermediate scores, e.g., 3.5, were given when appropriate.

Four fatty acid compounds were tested at five rates in triplicate, with a formulation blank. Viability was scored at 3 minutes, 30 minutes, and 1 hour after compound addition. Viability scores of triplicate samples were averaged.

The compounds tested were methyl ester of pelargonic acid (C9) (PAME), ethylene glycol ester of pelargonic acid (C9) (PAEGE), pelargonic acid (C9) (PA), and methyl ester of lauric acid (C12) (LAME). The results of this test are shown in Table 1.

The most toxic fatty acid to the nematode species tested was PAME (methyl ester of pelargonic acid; C9), with nearly complete kill at 0.005% at 3 minutes and complete kill at this concentration after 30 minutes. At the 30 minute time point, the second most nematicidal compound tested was LAME (methyl ester of lauric acid; C12). This compound killed more completely, but slightly more slowly than PAEGE (ethylene glycol ester of pelargonic acid; C9).

TABLE 1

*Caenorhabditis elegans* results

| Compound | Concentration | 3 min | 30 min | 1 hour |
|---|---|---|---|---|
| PAME (C9-methyl ester) | 0.1% | 4.0 | 5.0 | 5.0 |
| | 0.05% | 4.0 | 5.0 | 5.0 |
| | 0.025% | 4.0 | 5.0 | 5.0 |
| | 0.005% | 4.0 | 5.0 | 5.0 |
| | 0.0025% | 3.7 | 4.8 | 4.8 |
| PAEGE (C9-ethylene glycol ester) | 0.1% | 3.8 | 5.0 | 5.0 |
| | 0.05% | 3.2 | 4.7 | 4.7 |
| | 0.025% | 3.0 | 4.5 | 4.5 |
| | 0.005% | 1.2 | 2.5 | 2.7 |
| | 0.0025% | 1.0 | 2.0 | 2.2 |
| PA (C9-free acid) | 0.1% | 4.0 | 5.0 | 5.0 |
| | 0.05% | 1.5 | 4.7 | 4.7 |
| | 0.025% | 1.2 | 2.3 | 2.8 |
| | 0.005% | 1.5 | 1.5 | 3.5 |
| | 0.0025% | 1.5 | 1.5 | 3.7 |
| LAME (C12-methyl ester) | 0.1% | 2.2 | 5.0 | 5.0 |
| | 0.05% | 2.5 | 4.5 | 4.8 |
| | 0.025% | 2.5 | 4.8 | 5.0 |
| | 0.005% | 2.0 | 4.7 | 4.7 |
| | 0.0025 | 1.3 | 2.8 | 3.8 |
| Formulation | blank | 1.0 | 2.5 | 3.2 |
| Water | blank | 1.0 | 1.5 | 1.8 |

EXAMPLE 3

Phytotoxicity Evaluations

Phytotoxicity tests were done in two ways. First, 25 ml of 0.2% fatty acid solutions, or 1/10 diluted surfactant control, were carefully added by pipette to the soil of tomato plantlet soil "six-packs," each about 4–5" high. This quantity of liquid was sufficient to cause a slight amount of runoff. Care was taken to avoid application to stems or leaves, in order to determine the effects on plantlet roots.

Second, 5 ml of 0.2% fatty acid solutions, or 1/10 diluted surfactant control, were pipetted on the leaves, though much of the material ran off. All tomato plants were placed in regulated growth chambers, at 75° C., on a 16-hour light/8 hour dark cycle.

Tomato plants treated with fatty acids or surfactant controls were scored 40 hours after application. The only effects seen were with the highest rates of pelargonic acid (PA). At a 0.2% rate in soil, plant stems lost turgor and the plantlets drooped, though no browning was seen. The same concentration applied directly to leaves causes obvious wilting, though again no necrotic lesions were observed.

None of the other fatty acid treatments, even at the highest rates tested (0.2%) had any apparent effects on tomato plants. With PAME and LAME, at least 40-fold higher concentrations are required for phytotoxicity than for complete nematode kill in 30 minutes. Thus, the fatty acid ester compositions of the subject invention have an excellent "therapeutic ratio" for control of nematodes.

EXAMPLE 4

Fatty Acid Microemulsions

The following microemulsions can be utilized according to the subject invention for the control of nematodes:

| 1. Methyl pelargonate (nonanoate) | |
|---|---|
| Methyl nonanoate | 1.00% |
| Igepal CO 630 | 2.00% |
| Water | 85.00% |
| Isopropyl alcohol | 12.00% |
| 2. Ethylene glycol pelargonate (mono ester) | |
| Ethylene glycol pelargonate | 1.00% |
| Igepal CO 630 | 2.00% |
| Water | 85.00% |
| Isopropyl alcohol | 12.00% |
| 3. Methyl laurate | |
| Methyl laurate | 1.00% |
| Igepal CO 630 | 2.00% |
| Water | 92.00% |
| Isopropyl alcohol | 5.00% |
| 4. Pelargonic acid | |
| Pelargonic acid | 1.00% |
| Igepal CO 630 | 7.80% |
| Water | 79.00% |
| Isopropyl alcohol | 12.00% |
| 5. Methyl soyate | |
| Methyl soyate | 1.00% |
| Igepal CO 630 | 5.00% |
| Water | 95.00% |

The active ingredients can be mixed with a surfactant such as Igepal CO 630 or any other member of the same family of surfactants having greater of lesser degrees of ethyoxylation. These surfactants are well known to those skilled in the art. Water is then added with vigorous stirring, and then isopropyl alcohol or other appropriate co-solvent is added. In the case of methyl soyate, no co-solvent was required to develop the microemulsion.

The major reason for using relatively low concentration microemulsions as the "starting" concentrate is to ensure that, upon dilution, a microemulsion is still retained. Higher concentration concentrates when diluted will generally result in colloidal emulsions that defeat the purpose. This composition ensures that a microemulsion reaches the nematode rather than a much larger, less "solubilized" fatty acid ester active ingredient. The microemulsified fatty acid dimensions are much closer to molecular dimensions and, as such, functions much like a "water soluble" component.

All five of these microemulsion preparations were highly stable, and maintained a completely transparent and clear appearance at room temperature. Earlier work, a exemplified by Tarjan & Cheo, supra, showed decreeing nematicidal activity as the emulsion appearance changed with increasing emulsifier concentration from white opaque to semi-transparent to transparent to completely clear. Thus, the biological activity obtained with the microemulsion technology of the subject invention was an unexpected result that is against the previous teachings.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for controlling nematodes, wherein said method comprises applying to said nematodes an effective amount of a composition comprising a fatty acid ester an ethylene glycol ester of $C_9$ to $C_{12}$ fatty acids.

2. The method, according to claim 1, wherein said ester is applied as an aqueous microemulsion.

3. The method, according to claim 1, wherein said ester is applied at a concentration of about 0.001% to about 2%.

4. The method, according to claim 3, wherein said ester is applied at a concentration of about 0.05% to about 0.5%.

5. The method, according to claim 1, wherein said ester is applied in conjunction with a second nematicidal agent.

6. The method, according to claim 5, wherein said second nematicidal agent is selected from the group consisting of avermectins, ivermectin, and milbemycins.

7. The method, according to claim 6, wherein said avermectin, ivermectin, or milbemycin is present at a concentration between about 3 ppm and about 110 ppm.

8. The method, according to claim 6, wherein said avermectin, ivermectin, or milbemycin is applied at a rate of about 0.0006 lbs/acre to about 0.02 lbs/acre.

9. The method, according to claim 1, wherein said ester is applied at a rate of at least about 0.02 lb/acre.

10. The method, according to claim 1, wherein said composition further comprises a free fatty acid or fatty acid salt.

* * * * *

UNITED STATES PATENT AND TRADEMARK OFFICE
CERTIFICATE OF CORRECTION

PATENT NO. : 5,674,897

DATED : October 7, 1997

INVENTOR(S) : Kim *et al.*

It is certified that error appears in the above-identified patent and that said Letters Patent is hereby corrected as shown below:

Column 3, line 5: "*J. Nematol* 7:58-65" should read --*J. Nematol.* 7:58-65--;

line 8: "buryrio" should read --butyric--.

Column 4, line 28: "laurie" should read --lauric--.

Column 9, line 11: "a exemplified" should read --as exemplified--.

Signed and Sealed this

Twentieth Day of January, 1998

BRUCE LEHMAN

*Attest:*

*Attesting Officer*      Commissioner of Patents and Trademarks